(12) United States Patent
Shen

(10) Patent No.: US 10,391,328 B2
(45) Date of Patent: Aug. 27, 2019

(54) MULTI-WAVE SIGNAL KEEP-FIT ENERGY CHAMBER

(71) Applicant: Cunzheng Shen, Gansu (CN)

(72) Inventor: Cunzheng Shen, Gansu (CN)

(*) Notice: Subject to any disclaimer, the term of this patent is extended or adjusted under 35 U.S.C. 154(b) by 181 days.

(21) Appl. No.: 15/623,365

(22) Filed: Jun. 14, 2017

(65) Prior Publication Data

US 2017/0281963 A1    Oct. 5, 2017

Related U.S. Application Data

(63) Continuation of application No. PCT/CN2015/000770, filed on Nov. 9, 2015.

(30) Foreign Application Priority Data

Jan. 13, 2015  (CN) .......................... 2015 1 0014974

(51) Int. Cl.
*A61N 2/00* (2006.01)
*A61N 1/40* (2006.01)
*A61N 2/02* (2006.01)

(52) U.S. Cl.
CPC ............... *A61N 2/002* (2013.01); *A61N 1/40* (2013.01); *A61N 2/02* (2013.01)

(58) Field of Classification Search
CPC ............. A61N 1/40; A61N 2/002; A61N 2/02
See application file for complete search history.

*Primary Examiner* — Christine H Matthews
(74) *Attorney, Agent, or Firm* — Wayne & Ken, LLC; Tony Hom

(57) ABSTRACT

A multi-wave signal keep-fit energy chamber is provided. The keep-fit energy chamber is a multi-wave signal emission chamber. Multi-wave signal emission elements are uniformly distributed in the chamber. The multi-wave signal emission elements are subjected to signal modulation through a multi-wave signal modulation power supply under the action of an electric field and emit a multiple waveforms, thereby achieving the effects of eliminating human diseases, promoting health, prolonging life and keeping fit. The multi-wave signal modulation power supply manufactured by using a method for manufacturing the multi-wave signal modulation power supply is used for the multi-wave signal keep-fit energy chamber.

11 Claims, 15 Drawing Sheets

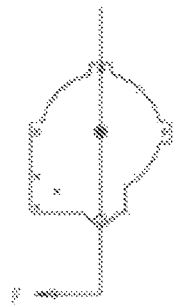
FIG. 5
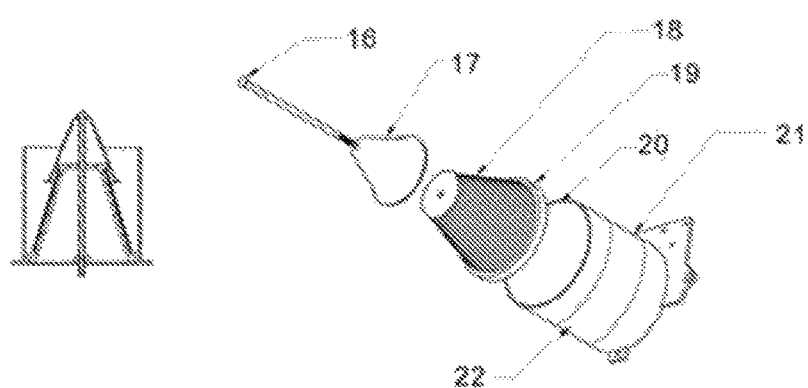
FIG. 4
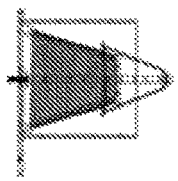
FIG. 7
FIG. 6

MULTI-WAVE SIGNAL KEEP-FIT ENERGY CHAMBER

TECHNICAL FIELD

The present invention belongs to the field of physical and medical health maintenance instruments and in particular relates to a multi-wave signal keep-fit energy chamber and a method for manufacturing a multi-wave signal modulation power supply.

BACKGROUND

The present invention belongs to a pioneering invention and is a keep-fit chamber consistent with biological multiple waveforms and a method for manufacturing a multi-wave signal modulation power supply. Organisms generate multi-wave resonance in the chamber, and through the multi-wave resonance, while human diseases such as diabetes, hypertension, gout, early-stage cancer, etc. can be treated in modern medicine and traditional Chinese medicine, rehabilitation is facilitated, and effects of promoting life cultivation and health preservation and prolonging life can be achieved.

According to the research on a human meridian system in many years by the inventor, the inventor discovers that the human meridian has multiple waveforms. More than 60 waveforms are observed from an oscilloscope, and 12 typical waveforms are taken as examples below, as shown in FIGS. 24-35. After researches and experiments of many years, waveforms of electromagnetic waves emitted by multi-wave signal emission elements of a multi-wave signal keep-fit energy chamber disclosed by the present invention are completely consistent with waveforms of electromagnetic waves emitted by the human meridians, so that the multi-wave signal keep-fit energy chamber disclosed by the present invention is manufactured by using the multi-wave signal emission elements. Therefore, a human body in the chamber generates the multi-wave resonance which contributes to rehabilitation of human diseases, health maintenance and prolongation of life. In addition, the present invention relates to a method for manufacturing a multi-wave signal modulation power supply. The multi-wave signal modulation power supply manufactured by using the method for manufacturing the multi-wave signal modulation power supply is used for the multi-wave signal keep-fit energy chamber.

SUMMARY

In order to solve the problem of treatment of human diseases such as diabetes, hypertension, gout, early-stage cancer and the like in modern medicine and traditional Chinese medicine as well as problems of rehabilitation, life cultivation and health preservation and prolongation of life, the present invention provides the following technical solution:

A multi-wave signal keep-fit energy chamber comprises a chamber shell, a middle squirrel-cage chamber framework, chamber opening/closing doors and multi-wave signal emission elements, wherein the multi-wave signal emission elements comprise a multi-wave signal emission element bracket, heating coils, a high-voltage electric field, a multi-wave signal modulation power supply, a multi-wave signal waveguide cover and a multi-wave signal emission element base; the heating coils are uniformly coiled on the multi-wave signal emission element bracket and used for heating the multi-wave signal emission elements; the top of the multi-wave signal emission element bracket is connected with the multi-wave signal waveguide cover; a bolt is connected with the top of the multi-wave signal emission element bracket from the top of the multi-wave signal waveguide cover to the multi-wave signal emission element base at the bottoms of the multi-wave signal emission elements; the multi-wave signal emission element base is electrically connected with a high-voltage positive pole; the bolt connected with the multi-wave signal waveguide cover is electrically connected with a high-voltage negative pole; a layer of multi-wave signal modulation power supply coils or metal bodies is coiled on an outer wall of the multi-wave signal emission element base to serve as a carrier of multi-wave signal charge of the multi-wave signal modulation power supply; the opening/closing doors are arranged at the front and rear parts of the middle squirrel-cage chamber framework; the exterior of the middle squirrel-cage chamber framework is coated by the chamber shell, and the interior of the middle squirrel-cage chamber framework is filled with porous liners; 90-150 multi-wave signal emission elements are uniformly distributed on the middle squirrel-cage chamber framework; a ventilating fan I, a ventilating fan II and lighting equipment are arranged in the chamber; a circuit control system of the multi-wave signal emission elements can clearly observe whether operations of the heating coil of each of the multi-wave signal emission elements, the high-voltage electric field and the multi-wave signal modulation power supply are normal or not on a monitoring screen by virtue of a software control program and can also observe and control temperature change in the energy chamber; and multi-wave resonance is generated between the multi-wave signal keep-fit energy chamber and a human body under the control of a running program.

The multi-wave signal emission element bracket is conical; the cone has a top diameter of 46 mm, a vertical height of 90 mm and a wall thickness of 4-5 mm; the multi-wave signal emission element bracket has a middle diameter of 77 mm and is a heating coil winding area; a conical bottom diameter of the multi-wave signal emission element bracket is 98 mm; a bolt hole for connecting the bolt is formed in the middle of a center circle; the diameter of the bolt hole in the top of a section of the multi-wave signal emission element bracket is 6 mm; a cone angle in a cavity of the multi-wave signal emission element bracket is 34 degrees; the multi-wave signal emission element bracket is made from violet sand earthenware and manufactured by glazing a main body surface by taking a TDP material as glaze and firing.

The power of the heating coils is 10-25 W.

The multi-wave signal waveguide cover is conical, is made of metals and has a height of 59-65 mm, a top diameter of 10-20 mm, a bottom diameter of 68-75 mm and a wall thickness of 1.5-3 mm; a bolt hole has a diameter of 6 mm; a cone angle in the cover is 34 degrees; and preferably, the multi-wave signal waveguide cover is made of stainless steel.

The multi-wave signal emission element base is made of plastics and has a diameter of 108-115 mm and a height of 107-115 mm; an inner wall of the base is a metal body; an outer concave hole of a bottom bolt hole has a diameter of 13 mm; an inner bolt hole has a diameter of 6 mm; and the multi-wave signal emission element base is electrically connected with a 1000-3000V high-voltage positive pole.

Coils or metal bodies coiled on the outer wall of the multi-wave signal emission element base have a height of 30-40 mm; and the carrier of the multi-wave signal charge has signal current of 2-3 mA and a voltage of 5-6V.

The middle squirrel-cage chamber framework has a diameter of 800-900 mm and a length of 2000-2100 mm; and a movable bed is arranged in the center of the middle squirrel-cage chamber framework and has a length of 1800 mm-1900 mm.

The negative pole of the multi-wave signal emission elements is a negative pole made from a magnesium material or magnesium alloy material sheets and has a thickness of 0.2-1 mm; the surface of the negative pole is insulated; a negative pole welding point and a welding point of a negative pole outgoing line are arranged on the negative pole of the multi-wave signal emission elements; and signal modulation electrodes and collectors of the multi-wave signal emission elements comprise a collector I, a negative pole plate, a collector II, a copper or silver foil electrode I on the collector, a copper or silver foil electrode II on the collector, and a positive pole outgoing line.

The multi-wave signal modulation power supply has a specification of 40.5×32.5×18.5 cm and a mass of 30 kg; a multi-wave signal modulation power supply coil is wound on the multi-wave signal modulator power supply; a positive pole binding post and a negative pole binding post are arranged on the multi-wave signal modulation power supply; an "inspection report" has been issued for the multi-wave signal modulation power supply by National Power Supply Product Quality Supervision and Testing Center by virtue of a product name of a zero-point multifunctional physical power supply, and the report number is (2014) QTW104.

In the multi-wave signal keep-fit energy chamber, chamber external dimension parameters comprise: a height of 1400-1600 mm, a length of 2100-2400 mm and a diameter of 96-110 mm; power consumption parameters comprise: operating voltages of 36V and 12V, a frequency of 50-60 Hz and high voltage of 1000-3000V in a direct-current electric field of the emission elements; total power consumption is 300-4000 W; and an operating temperature of 33° C.-50° C. in the chamber is adjustable and controllable. The heating coils of the 90-150 multi-wave signal emission elements, the multi-wave signal modulation power supply, the high-voltage electric field, the operating temperature in the chamber and whether an operating state is normal or not can be clearly reflected on a system control screen, as shown in figures.

A circuit control system of the multi-wave signal keep-fit energy chamber is shown in FIG. 36, and a specific process is as follows: a system power supply outputs an AC 220V voltage to a voltage conversion circuit, the voltage conversion circuit converts the voltage into an AC 0-36V adjustable voltage to be supplied to the heating coils and also supplies a voltage of DC 6-12V to a voltage generator; the heating coils, the voltage generator and the multi-wave signal power supply are supplied to a controller; and the controller controls the 90-150 emission elements by virtue of instructions of a software system on a computer, so that whether operations of the heating coil of each of the emission elements, the high-voltage electric field and the multi-wave signal modulation power supply are normal or not can be controlled, and a temperature change in the chamber can also be observed and controlled.

A manufactured multi-wave signal modulation power supply comprises a negative pole made of magnesium and magnesium alloy sheets, wherein the sheets have a thickness of 0.2-1 mm; the surface of each of the sheets is insulated.

A copper or silver foil is attached to the collector to serve as a positive pole. A voltage between the positive pole and the negative pole is 1.3-2V; individual collector plates are superposed and connected with one another; and the signal current of the carrier of the multi-wave signal charge is satisfied so as to meet the requirements of current of 90-270 mA and voltage of 5-6V.

The collector is manufactured in the following manner:

emulsifying the following nine materials: (1) 600 g of calcium chloride soaked into glue in 600 g of water; (2) 7000 g of 2% xanthan gum aqueous solution; (3) 1800 g of industrial salt; (4) 360 g of wool fat; (5) 360 g of glycerin; (6) 300 g of vegetable oil; (7) 600 g of 133 water-soluble glue; (8) 1800 g of 10% glutinous rice flour paste and (9) 300 g of a lipophilic emulsifier;

adding (10) 240 g of thorium oxide, (11) 240 g of iron phosphate, (12) 100 g of lithium cobalt oxides, (13) 100 g of lithium nickelate, (14) 4800 g of trisodium phosphate, (15) 300 g of industrial salt, (16) 800-1200 g of cobalt sulfate and (17) 3600-4100 g of graphite into the emulsified mixture; and uniformly stirring by a stirrer, coating on 20-30 g of paper with a thickness of 0.3-0.6 mm, drying, slicing, sizing, adhering to a negative pole with a corresponding size, performing vacuum treatment at a temperature of 40-70° C. for 1-2 hours, drying to obtain the product.

The present invention has the beneficial technical effects that:

The multi-wave signal keep-fit energy chamber is a multi-wave signal emission chamber, and 90-150 multi-wave signal emission elements are uniformly distributed in the chamber. The elements are subjected to signal modulation through a multi-wave signal power supply under the action of an electric field and emit a multiple waveforms corresponding to a human body to enable the human body to generate multi-wave resonance in the chamber, thereby achieving the effects of eliminating human diseases, promoting health, prolonging life and keeping fit. The multi-wave signal modulation power supply manufactured by using a method for manufacturing the multi-wave signal modulation power supply can be applied to the multi-wave signal keep-fit energy chamber.

BRIEF DESCRIPTION OF DRAWINGS

FIG. 4 is an assembly diagram of multi-wave signal emission elements;

FIG. 5 is a sectional view of an assembly diagram of multi-wave signal emission elements;

FIG. 6 is an upward view of multi-wave signal emission elements;

FIG. 7 is an F-F sectional view;

Figure 1:
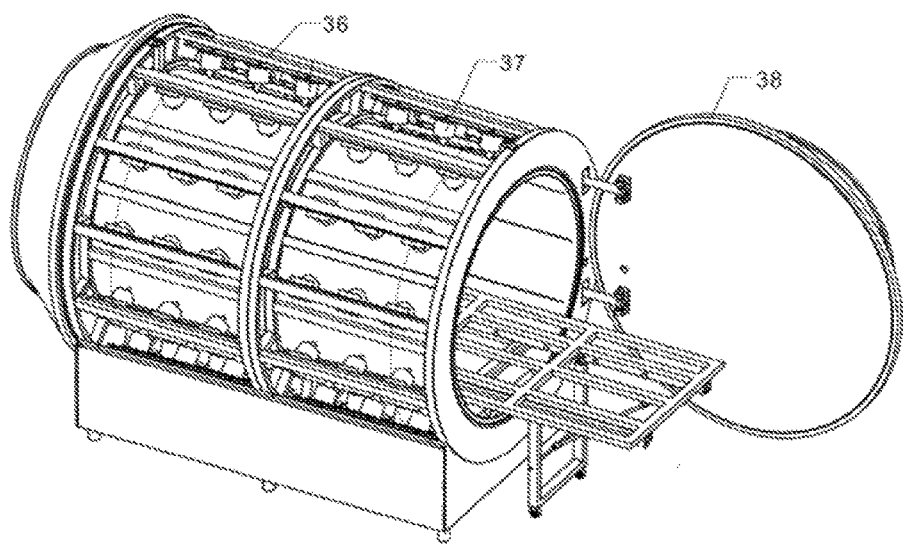
FIG. 1 is a perspective structural diagram of a multi-wave signal keep-fit energy chamber.
Figure 2:
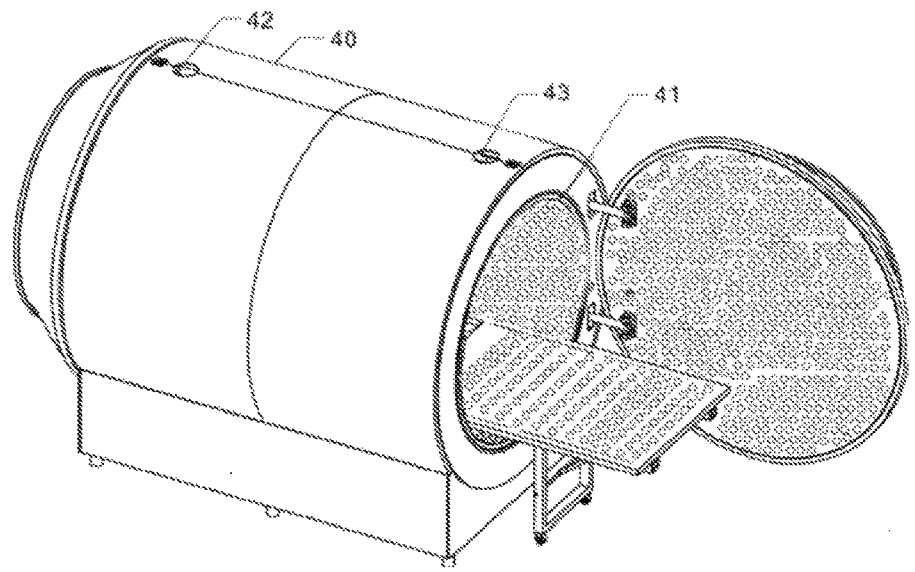
FIG. 2 is a structural general drawing of a multi-wave signal keep-fit energy chamber.
Figure 3:
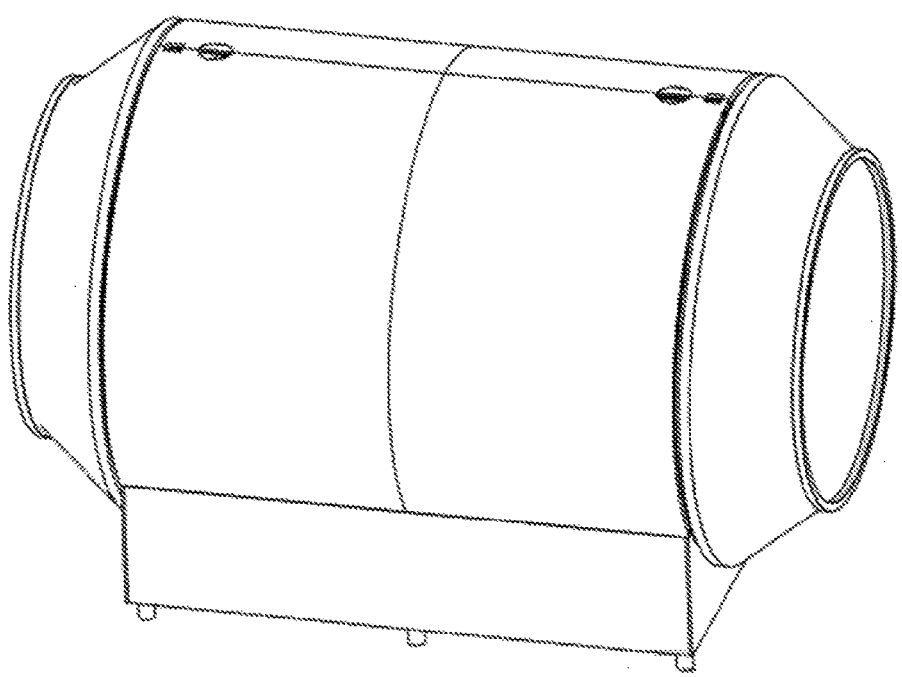
FIG. 3 is a structural closed diagram of a multi-wave signal keep-fit energy chamber.
Figure 8:
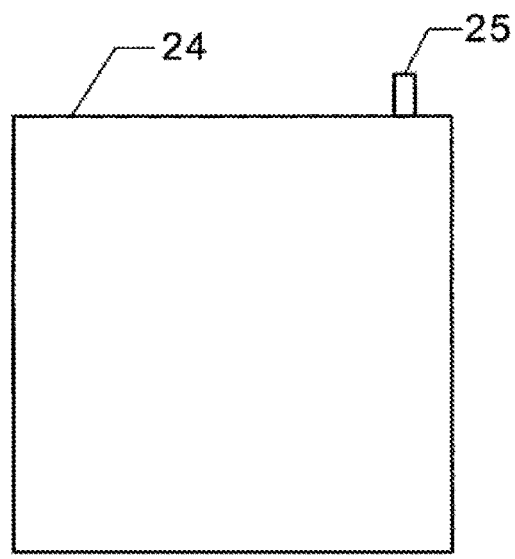
FIG. 8 is a negative pole diagram of a multi-wave signal modulation power supply.
Figure 9:
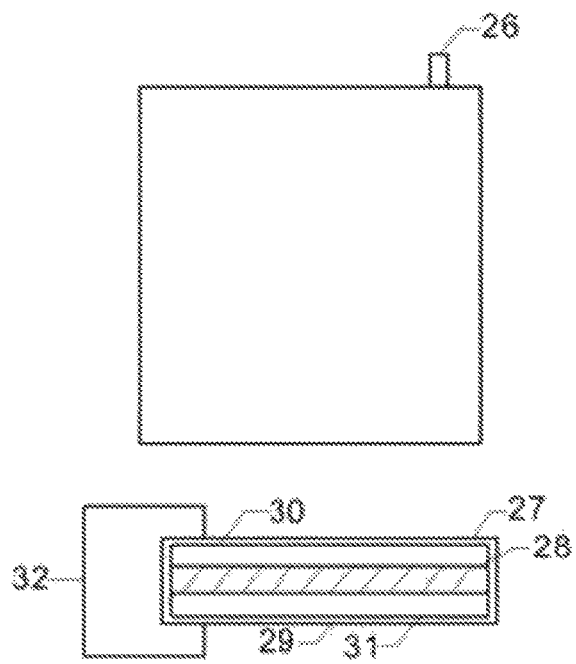
FIG. 9 is a direct bonding sectional view of a modulation pole and a negative pole of a multi-wave signal modulation power supply.
Figure 10:
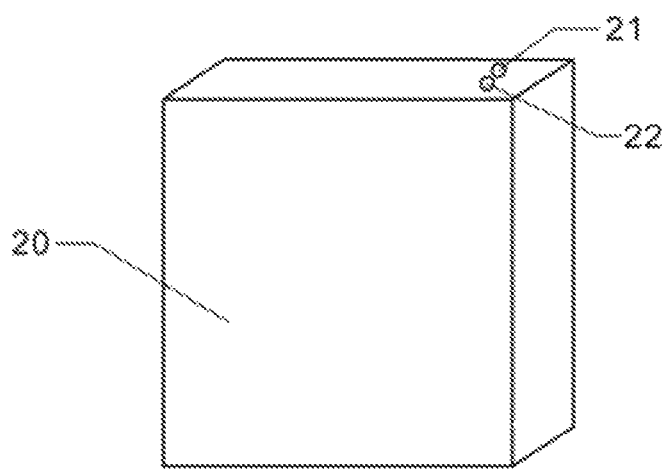
FIG. 10 is a structural diagram of a multi-wave signal modulation power supply.
Figure 11:
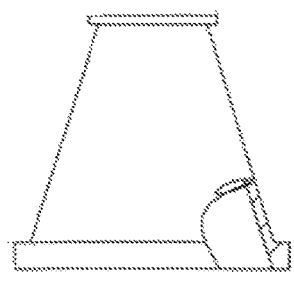
FIG. 11 is a front view of a multi-wave signal emission element bracket.
Figure 12:
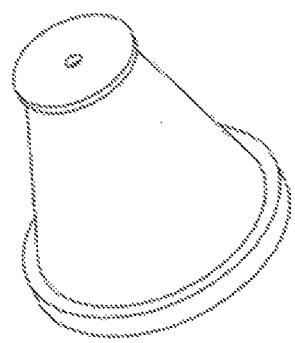
FIG. 12 is a three-dimensional stereogram of a multi-wave signal emission element bracket.
Figure 13:
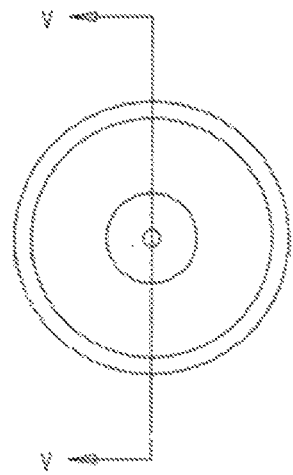
FIG. 13 is a bottom structural diagram of a multi-wave signal emission element bracket.
Figure 14:
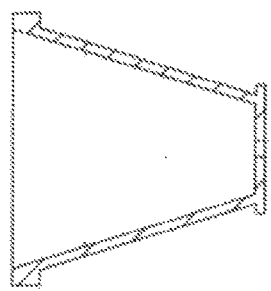
FIG. 14 is an F-F sectional view of a multi-wave signal emission element bracket.
Figure 15:
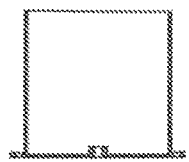
FIG. 15 is a front sectional view of a multi-wave signal emission element base.
Figure 16:
FIG. 16 is an installation angle sectional view of a multi-wave signal emission element base.
Figure 17:
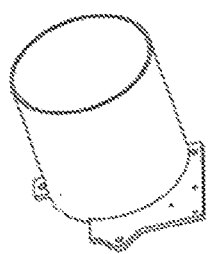
FIG. 17 is a three-dimensional structural diagram of a multi-wave signal emission element base.
Figure 18:
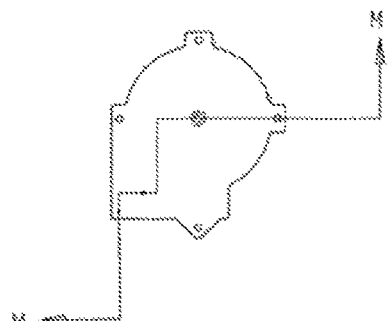
FIG. 18 is a bottom structural diagram of a multi-wave signal emission element base.
Figure 19:
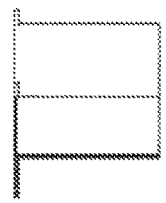
FIG. 19 is an M-M surface sectional view of a multi-wave signal emission element base.
Figure 20:
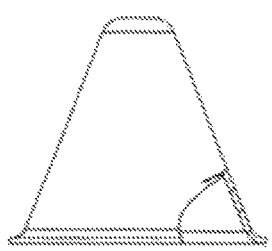
FIG. 20 is a sectional view of a multi-wave signal waveguide cover.
Figure 21:
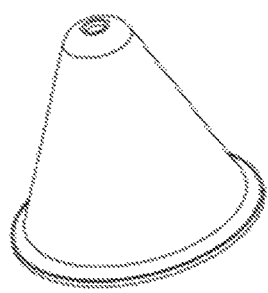
FIG. 21 is a bottom structural diagram of a multi-wave signal waveguide cover.
Figure 22:
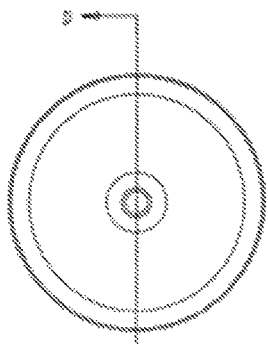
FIG. 22 is a three-dimensional structural diagram of a multi-wave signal waveguide cover.
Figure 23:
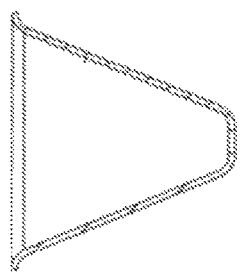
FIG. 23 is a D-D sectional view of a multi-wave signal waveguide cover.
Figure 24:
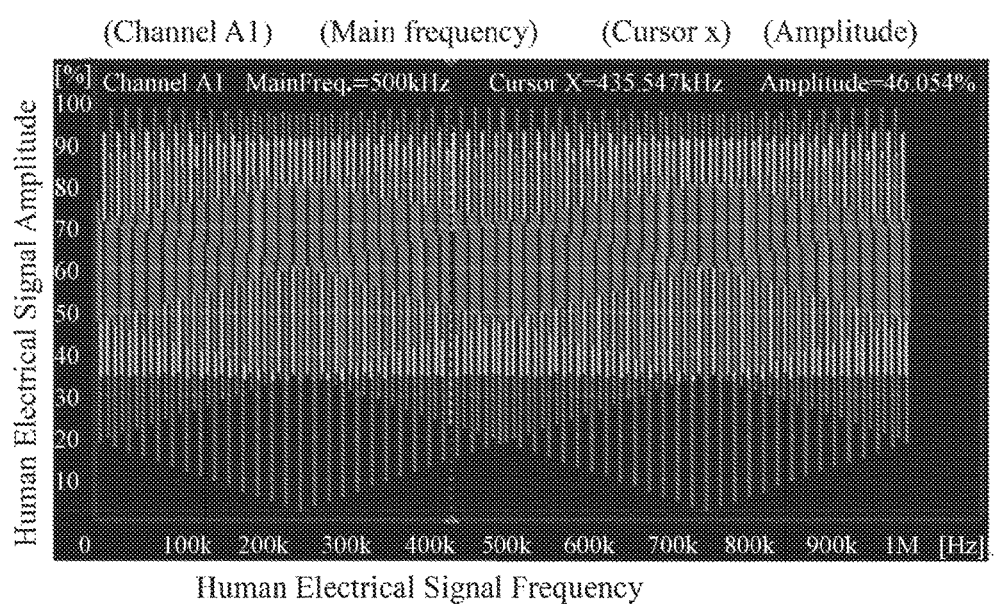
FIG. 24 is a human electric signal oscillogram I.
Figure 25:
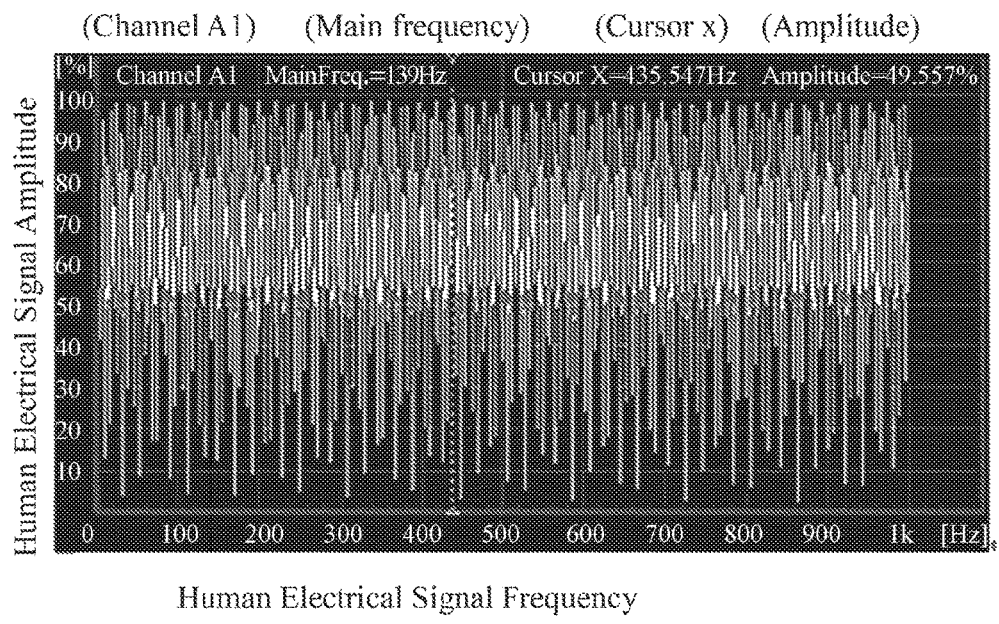
FIG. 25 is a human electric signal oscillogram II.
Figure 26:
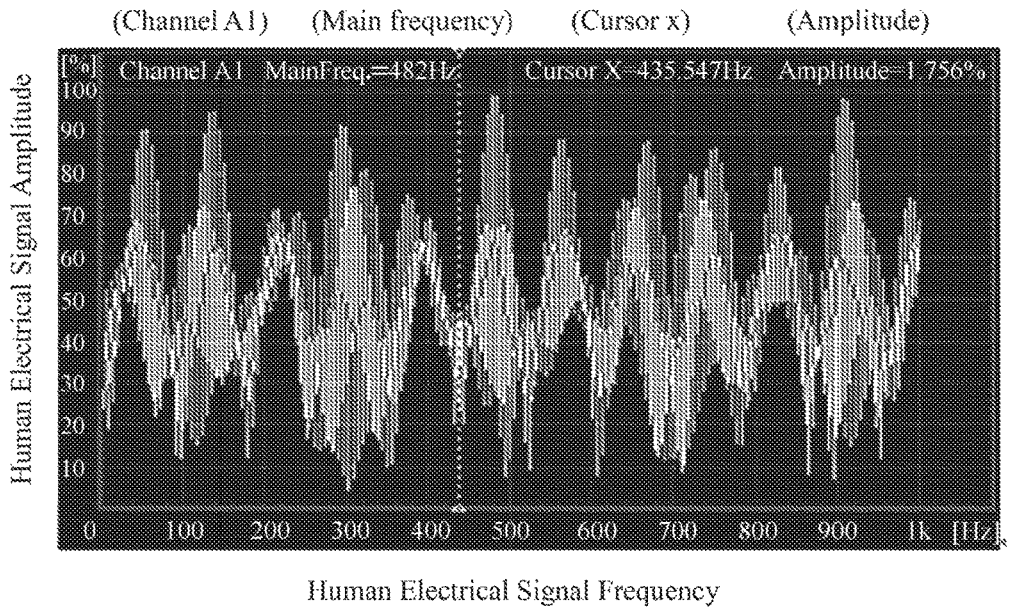
FIG. 26 is a human electric signal oscillogram III.
Figure 27:
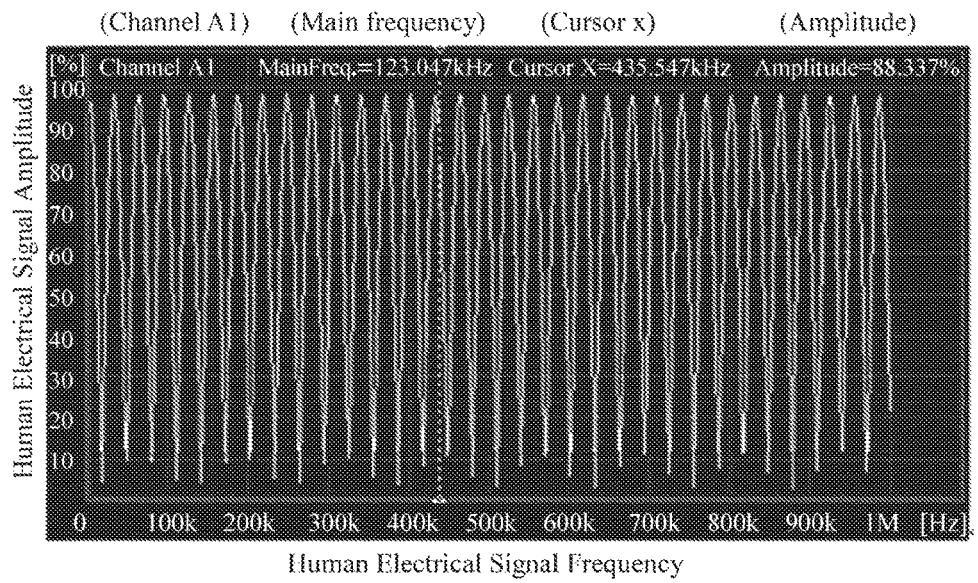
FIG. 27 is a human electric signal oscillogram IV.
Figure 28:
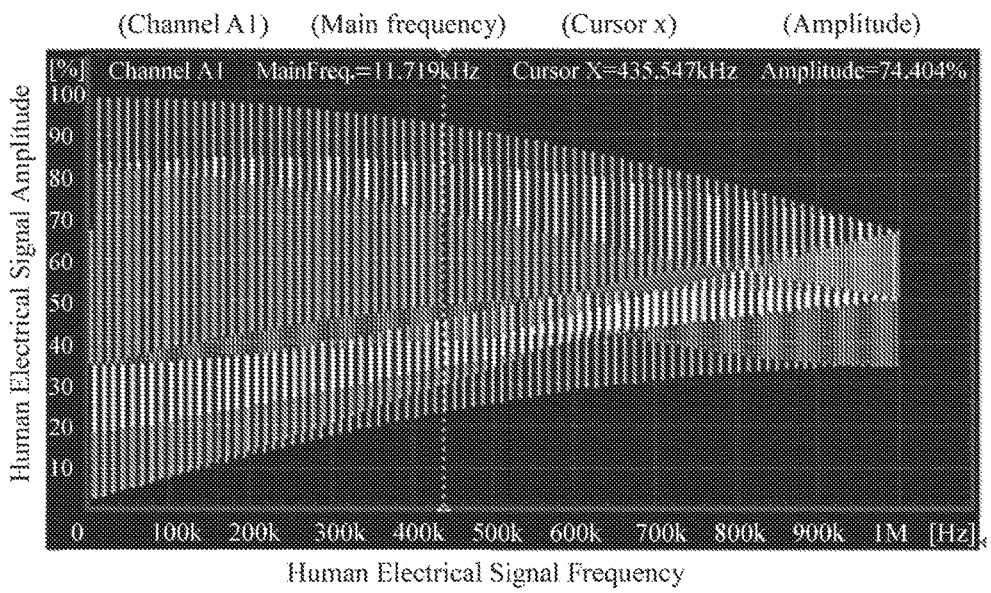
FIG. 28 is a human electric signal oscillogram V.
Figure 29:
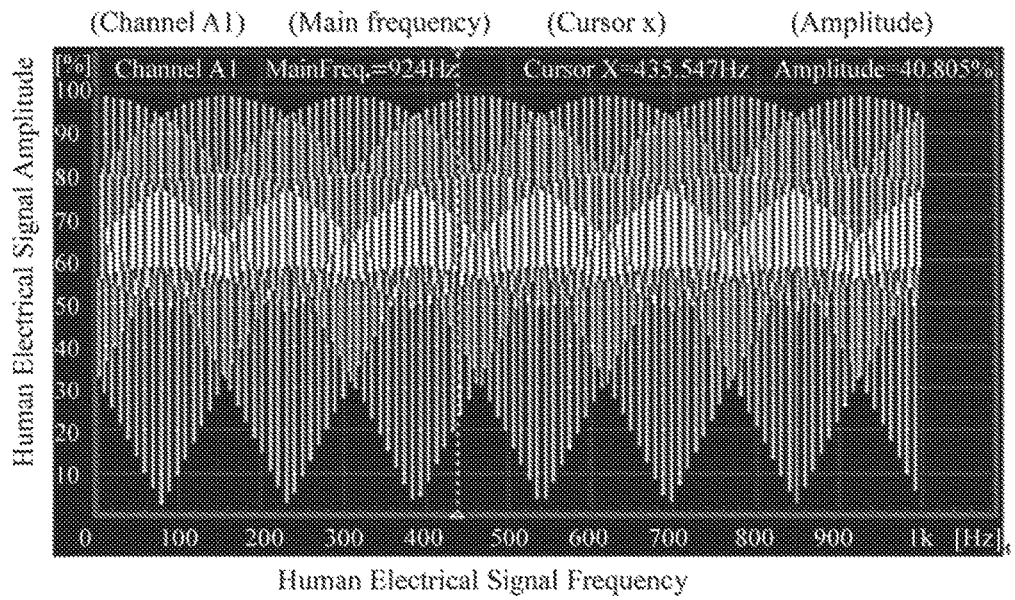
FIG. 29 is a human electric signal oscillogram VI.
Figure 30:
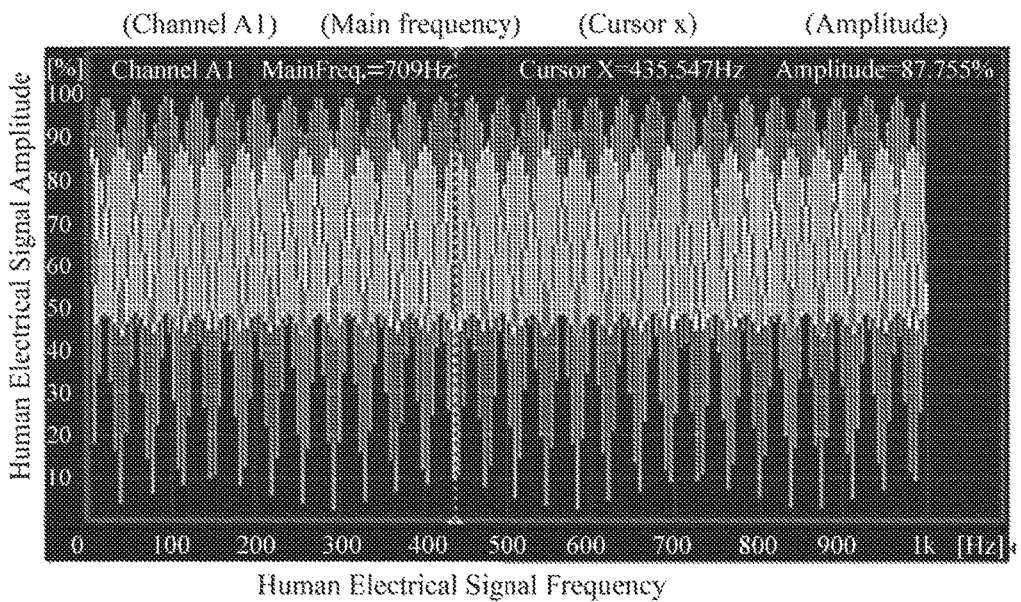
FIG. 30 is a human electric signal oscillogram VII.
Figure 31:
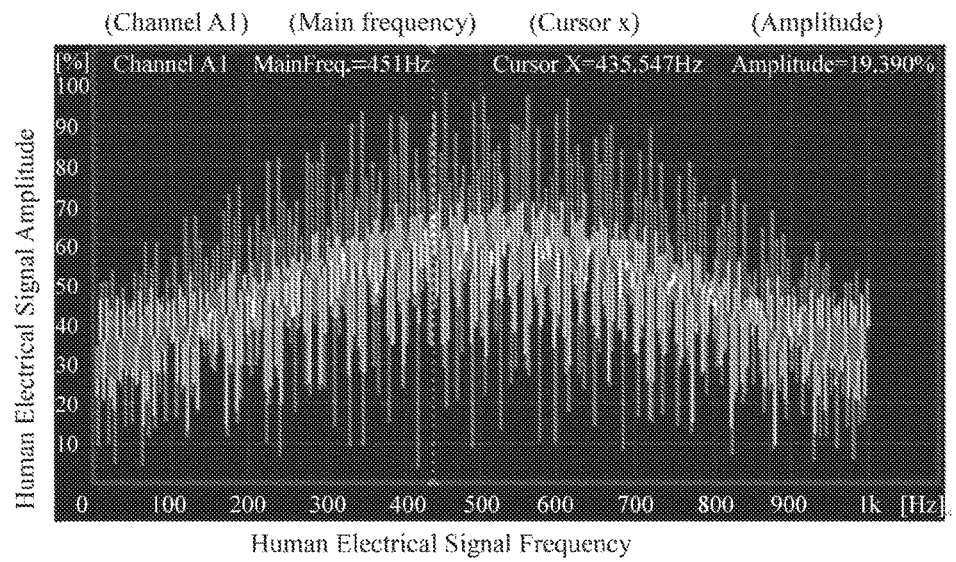
FIG. 31 is a human electric signal oscillogram VIII.
Figure 32:
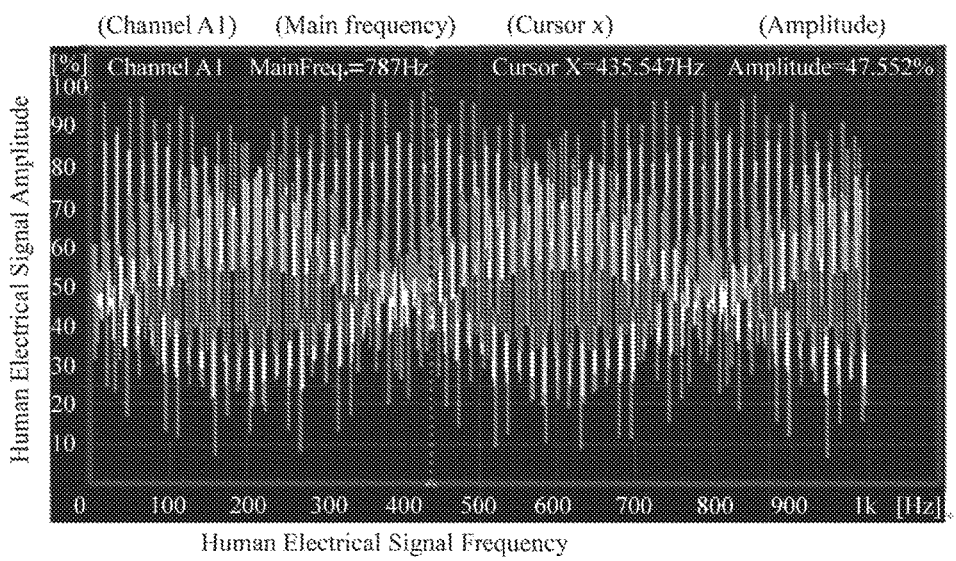
FIG. 32 is a human electric signal oscillogram IX.
Figure 33:
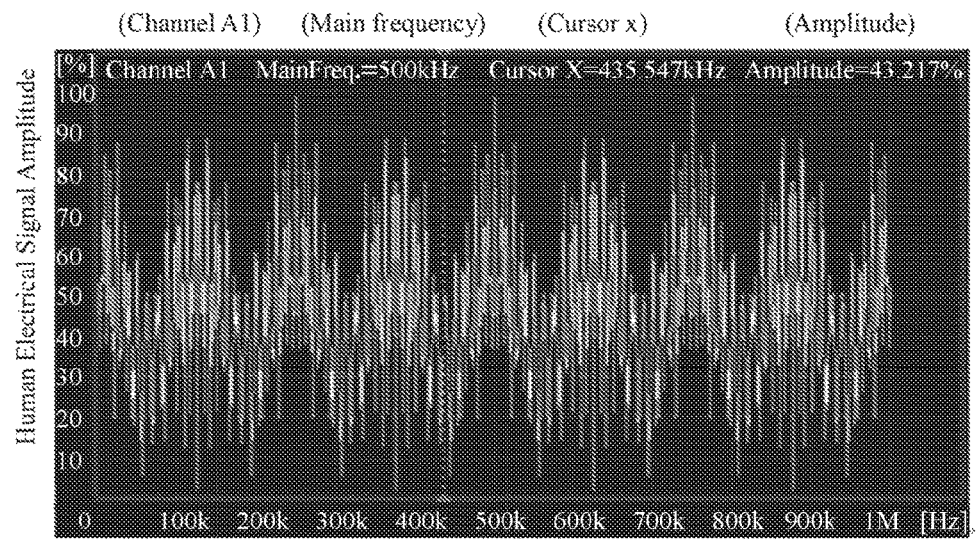
FIG. 33 is a human electric signal oscillogram X.
Figure 34:
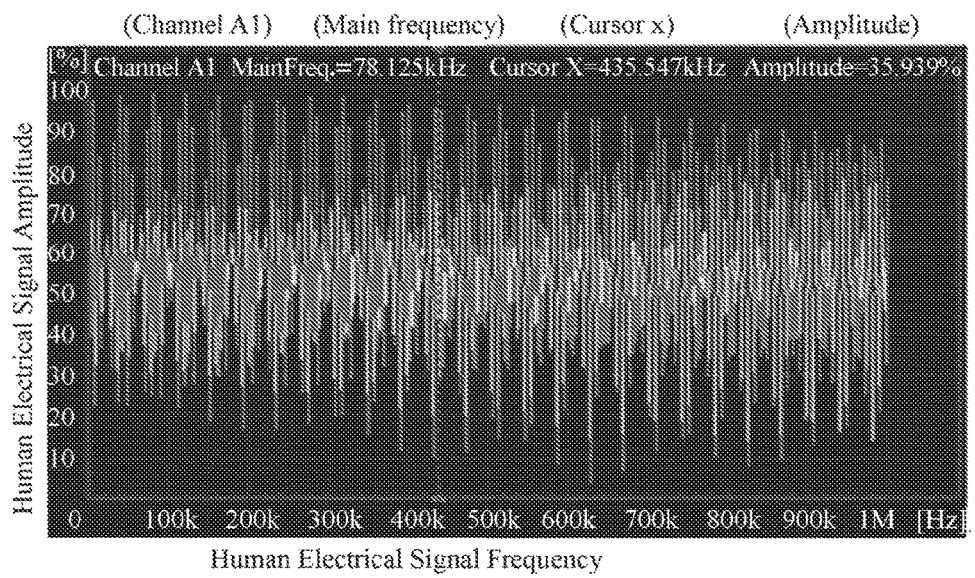
FIG. 34 is a human electric signal oscillogram XI.
Figure 35:
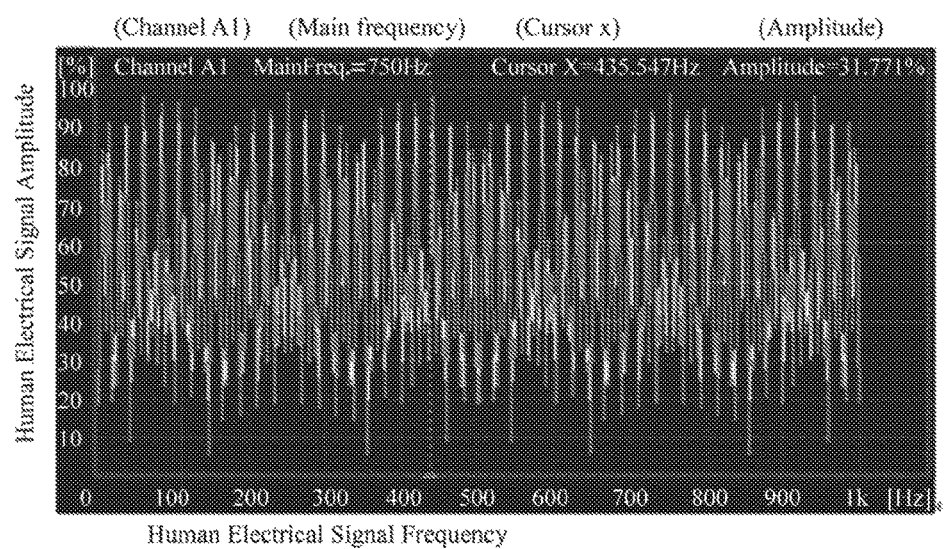
FIG. 35 is a human electric signal oscillogram XII.

DESCRIPTION OF ATTACHED DRAWINGS 16 bolt; 17 multi-wave signal waveguide cover; 18 heating coil; 19 multi-wave signal emission element bracket; 20 high-voltage electric field; 21 multi-wave signal emission element base; 22 multi-wave signal modulation power supply coil; 24 negative pole; 25 negative pole welding point; 26 welding point of negative pole outgoing line; 27 collector I; 28 negative pole plate; 29 collector II; 30 copper or silver foil electrode I on collector; 31 copper or silver foil electrode II on collector; 32 positive pole outgoing line; 33 multi-wave signal modulation power supply; 34 positive pole binding post; 35 negative pole binding post; 36 middle squirrel-cage chamber framework; 37 multi-wave signal emission element; 38 chamber opening/closing door; 39 movable bed; 40 chamber shell; 41 porous liner; 42 ventilating fan I; and 43 ventilating fan II.

DETAILED DESCRIPTION

The present invention is further described below by combining drawings and preferred embodiments of the present invention.

As shown in FIGS. 1-10, a multi-wave signal keep-fit energy chamber comprises a chamber shell 40, a middle squirrel-cage chamber framework 36, chamber opening/closing doors 38 and multi-wave signal emission elements 37, wherein the multi-wave signal emission elements 37 comprise a multi-wave signal emission element bracket 19, heating coils 18, a high-voltage electric field 20, a multi-wave signal modulation power supply 33, a multi-wave signal waveguide cover 17 and a multi-wave signal emission element base 21; the heating coils 18 are uniformly coiled on the emission element bracket 19 and used for heating the multi-wave signal emission elements 37; the top of the multi-wave signal emission element bracket 19 is connected with the multi-wave waveguide cover 17; a bolt is connected with the top of the multi-wave signal emission element bracket 19 from the top of the multi-wave signal waveguide cover 17 to the multi-wave signal emission element base 21 arranged at the bottoms of the multi-wave signal emission elements 37; the multi-wave signal emission element base 21 is connected with a high-voltage positive pole; the bolt connected with the multi-wave signal waveguide cover 17 is connected with a high-voltage negative pole; a layer of coils or metal bodies is coiled on an outer wall of the equal micro particle emission element base 21 to serve as a carrier of multi-wave signal charge of the multi-wave signal modulation power supply 33; the chamber opening/closing doors are arranged at the front and rear parts of the chamber of the middle squirrel-cage chamber framework 36; the exterior of the chamber is coated by the chamber shell 40, and the interior is filled with porous liners 41; the movable bed 39 is arranged in the center; 90-150 emission elements 37 are uniformly distributed on the middle squirrel-cage chamber framework 36; a ventilating fan 142, a ventilating fan II 43 and lighting equipment are arranged in the chamber; a circuit control system of the equal-microparticle emission elements 37 can clearly observe whether operations of the heating coil 18 of each of the multi-wave signal emission elements, the high-voltage electric field 20 and the multi-wave signal modulation power supply 33 are normal or not on a monitoring screen by virtue of a software control program and can also observe and control temperature change in the energy chamber; and multi-wave resonance is generated between the multi-wave signal keep-fit energy chamber and a human body under the control of a running program.

As shown in FIGS. 11-14, the multi-wave signal emission element bracket 19 is conical; the cone has a top diameter of 46 mm, a vertical height of 90 mm and a wall thickness of 4-5 mm; the multi-wave signal emission element bracket 19 has a middle diameter of 77 mm and is a heating coil winding area; a conical bottom diameter of the multi-wave signal emission element bracket 19 is 98 mm; a bolt hole for connecting the bolt 16 is formed in the middle of a center circle; the diameter of the bolt hole in the top of a section of the multi-wave signal emission element bracket 19 is 6 mm; a cone angle in a cavity of the bracket is 34 degrees; the multi-wave signal emission element bracket 19 is made from violet sand earthenware and manufactured by glazing a main body surface by taking a TDP material as glaze and firing.

The power of the heating coils 18 is 10-25 W.

As shown in FIGS. 20-23, the multi-wave signal waveguide cover 17 is conical, is made of metals and has a height of 59-65 mm, a top diameter of 10-20 mm, a bottom diameter of 68-75 mm and a wall thickness of 1.5-3 mm; a bolt hole has a diameter of 6 mm; a cone angle in the cover is 34 degrees; and preferably, the multi-wave signal waveguide cover 17 is made of stainless steel.

As shown in FIGS. 15-19, the multi-wave signal emission element base 21 is made of plastics and has a diameter of 108-115 mm and a height of 107-115 mm; an inner wall of the base is a metal body; an outer concave hole of a bottom bolt hole has a diameter of 13 mm; an inner bolt hole has a diameter of 6 mm; and the multi-wave signal emission element base 21 is electrically connected with a 1000-3000V high-voltage positive pole. Coils or metal bodies coiled on the outer wall of the multi-wave signal emission element base 21 have a height of 30-40 mm; and the carrier of the multi-wave signal charge has signal current of 2-3 mA and a voltage of 5-6V.

The middle squirrel-cage chamber framework 36 has a diameter of 800-900 mm and a length of 2000-2100 mm; and a movable bed 39 arranged in the center of the middle squirrel-cage chamber framework 36 has a length of 1800 mm-1900 mm.

The circuit control system of the multi-wave signal emission elements 37 controls a temperature of the multi-wave signal keep-fit chamber to be between 33° C. and 50° C. to serve as a stable operating range.

The negative pole 24 of the multi-wave signal emission elements 37 is a negative pole made from a magnesium material or magnesium alloy material sheets and has a thickness of 0.2-1 mm; the surface of the negative pole is insulated; a negative pole welding point 25 and a welding point 26 of a negative pole outgoing line are arranged on the negative pole of the multi-wave signal emission elements; and signal modulation electrodes and collectors of the multi-wave signal emission elements 37 comprise a collector I 27, a collector II 29, a copper or silver foil electrode I 30 on the collector, a copper or silver foil electrode II 31 on the collector, and a positive pole outgoing line 32. The multi-wave signal modulation power supply 33 has a specification of 40.5×32.5×18.5 cm and a mass of 30 kg; a multi-wave signal modulation power supply coil 22 is wound on the multi-wave signal modulation power supply 33; a positive pole binding post 34 and a negative pole binding post 35 are arranged on the multi-wave signal modulation power supply 33; an "inspection report" has been issued for the multi-wave signal modulation power supply by National Power Supply Product Quality Supervision and Testing Center by virtue of a product name of a zero-point multifunctional physical power supply, and the report number is (2014)QTW104.

In the multi-wave signal keep-fit energy chamber, chamber external dimension parameters comprise: a height of 1400-1600 mm, a length of 2100-2400 mm and a diameter of 96-110 mm; power consumption parameters comprise: operating voltages of 36V and 12V, a frequency of 50-60 Hz and high voltage of 1000-3000V in a direct-current electric field of the emission elements; total power consumption is 300-4000 W; and an operating temperature of 33° C.-50° C. in the chamber is adjustable and controllable. The heating coils 18 of the 90-150 multi-wave signal emission elements, the multi-wave signal modulation power supply 33, the high-voltage electric field 20, the operating temperature in the chamber and whether an operating state is normal or not can be clearly reflected on a system control screen, as shown in figures.

Figure 36:
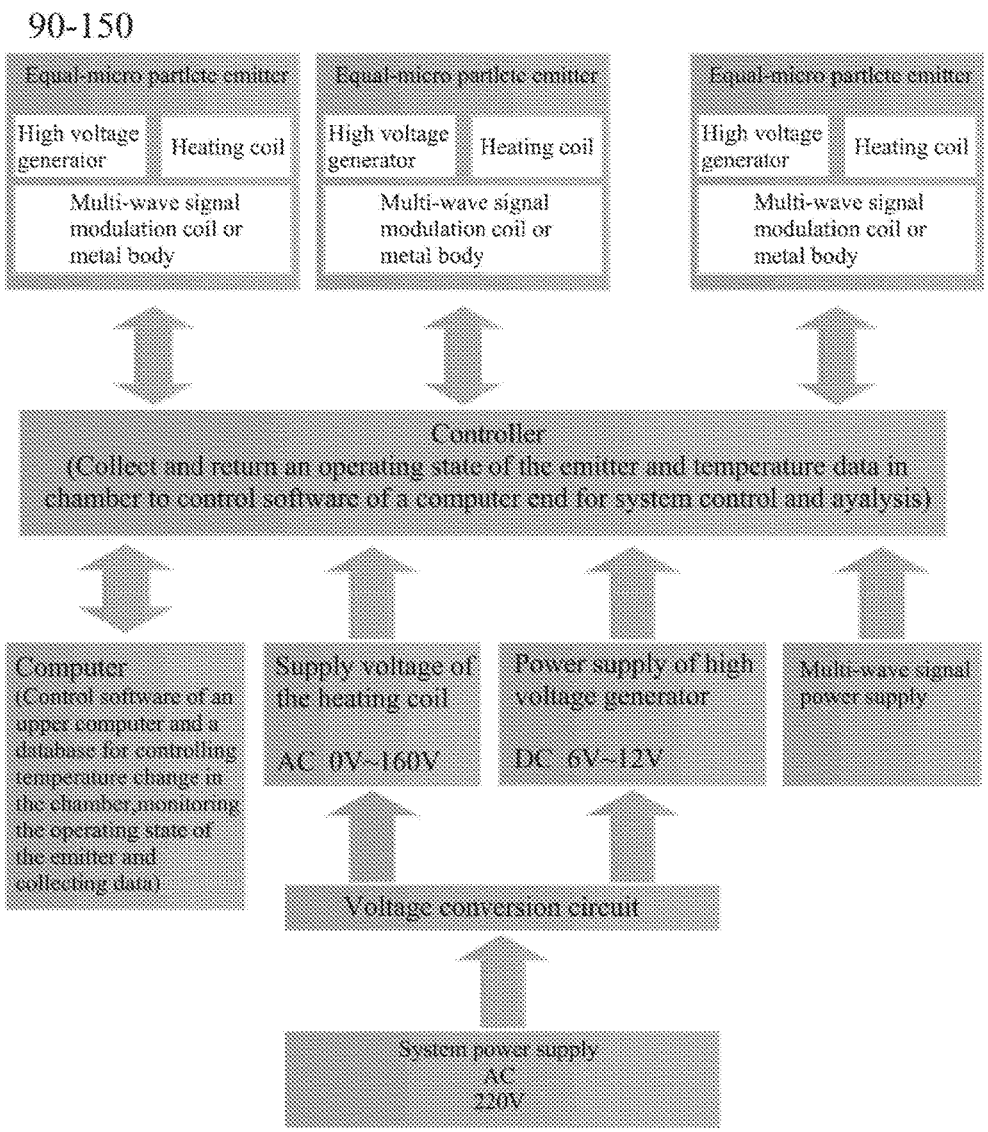
FIG. 36 is a structural diagram of a circuit control system of a keep-fit chamber.

A circuit control system of the multi-wave signal keep-fit energy chamber is shown in FIG. 36, and a specific process is as follows: a system power supply outputs an AC 220V voltage to a voltage conversion circuit the voltage conversion circuit converts the voltage into an AC 0-36V adjustable voltage to be supplied to the heating coils and also supplies a voltage of DC 6-12V to a voltage generator; the heating coils, the voltage generator and the multi-wave signal power supply are supplied to a controller; and the controller controls the 90-150 emission elements by virtue of instructions of a software system on a computer, so that whether operations of the heating coil of each of the emission elements, the high-voltage electric field and the multi-wave signal modulation power supply are normal or not can be controlled, and a temperature change in the chamber can also be observed and controlled.

A method for manufacturing the multi-wave signal modulation power supply 33 comprises the following manufacturing steps:

I, manufacturing a negative pole 24 of the multi-wave signal power supply from magnesium and magnesium alloy sheets, wherein the sheets have a thickness of 0.2-1 mm, and the surface of each of the sheets is insulated;

II, manufacturing the collector of the multi-wave signal modulation power supply 33:

emulsifying the following nine materials: (1) 600 g of calcium chloride soaked into glue in 600 g of water; (2) 7000 g of 2% xanthan gum aqueous solution; (3) 1800 g of industrial salt; (4) 360 g of wool fat; (5) 360 g of glycerin; (6) 300 g of vegetable oil; (7) 600 g of 133 water-soluble glue; (8) 1800 g of 10% glutinous rice flour paste and (9) 300 g of a lipophilic emulsifier; then adding (10) 240 g of thorium oxide, (11) 240 g of iron phosphate, (12) 100 g of lithium cobalt oxides, (13) 100 g of lithium nickelate, (14) 4800 g of trisodium phosphate, (15) 300 g of industrial salt, (16) 800-1200 g of cobalt sulfate and (17) 3600-4100 g of graphite into the emulsified mixture; and uniformly stirring all the materials above by a stirrer, coating on 20-30 g of paper with a thickness of 0.3-0.6 mm, drying, slicing, sizing, adhering to a negative pole with a corresponding size, performing vacuum treatment at a temperature of 40-70° C. for 1-2 hours, attaching a copper or silver foil onto the collector plates to serve as the positive pole. A voltage between the positive pole and the negative pole is 1.3-2V; individual collector plates are superposed and connected with one another; and the signal current of the carrier of the multi-wave signal charge is satisfied so as to meet the requirements of current of 90-270 mA and voltage of 5-6V.

The multi-wave signal keep-fit energy chamber is a multi-wave signal emission chamber, and 90-150 multi-wave signal emission elements are uniformly distributed in the chamber. The elements are subjected to signal modulation through a multi-wave signal modulation power supply under the action of an electric field and emit multiple waveforms corresponding to a human body so as to enable the human body to generate multi-wave resonance in the chamber, thereby achieving the effects of eliminating human diseases, promoting health, prolonging life and keeping fit. The multi-wave signal modulation power supply manufactured by using a method for manufacturing the multi-wave signal modulation power supply can be applied to the multi-wave signal keep-fit chamber.

The descriptions above are only preferred embodiments of the present invention, so the implementation scope of the present invention shall not be defined accordingly, i.e., equivalent changes and modifications made according to the patent scope and description contents of the present invention shall still belong to the coverage scope of the present invention.

What is claimed is:

1. A multi-wave signal keep-fit energy chamber, comprising a chamber shell, a middle squirrel-cage chamber framework, chamber opening/closing doors and multi-wave signal emission elements, wherein:

the multi-wave signal emission elements comprise a multi-wave signal emission element bracket, heating coils, a high-voltage electric field, a multi-wave signal modulation power supply, a multi-wave signal waveguide cover and a multi-wave signal emission element base;

the heating coils are uniformly coiled on the multi-wave signal emission element bracket and used for heating the multi-wave signal emission elements;

a top of the multi-wave signal emission element bracket is connected with the multi-wave signal waveguide cover;

a bolt is connected with the top of the multi-wave signal emission element bracket from a top of the multi-wave signal waveguide cover to the multi-wave signal emission element base at bottoms of the multi-wave signal emission elements;

the multi-wave signal emission element base is electrically connected with a high-voltage positive pole;

the bolt is electrically connected with a high-voltage negative pole;

a layer of multi-wave signal modulation power supply coils or metal bodies is coiled on an outer wall of the multi-wave signal emission element base to serve as a carrier of multi-wave signal charge of the multi-wave signal modulation power supply;

the chamber opening/closing doors are arranged at front and rear parts of the middle squirrel-cage chamber framework;

an exterior of the middle squirrel-cage chamber framework is coated by the chamber shell, and an interior of the middle squirrel-cage chamber framework is filled with porous liners;

a number of 90-150 of the multi-wave signal emission elements are uniformly distributed on the middle squirrel-cage chamber framework;

a first ventilating fan, a second ventilating fan and lighting equipment are arranged in the chamber; and a circuit control system of the multi-wave signal emission elements is adapted to monitor operations of the heating coils of each of the multi-wave signal emission elements, the high-voltage electric field and the multi-wave signal modulation power supply by virtue of a software control program, and the circuit control system is further adapted to monitor and control temperature change in the energy chamber.

2. The multi-wave signal keep-fit energy chamber according to claim 1, wherein the multi-wave signal emission element bracket is in a shape of a cone with a top diameter of 46 mm, a vertical height of 90 mm and a wall thickness of 4-5 mm; the multi-wave signal emission element bracket has a middle diameter of 77 mm and has a heating coil winding area in a middle area of the multi-wave signal emission element bracket; a conical bottom diameter of the multi-wave signal emission element bracket is 98 mm; a bolt hole for connecting the bolt is formed in the middle area; the diameter of the bolt hole in a top of a section of the multi-wave signal emission element bracket is 6 mm; a cone angle in a cavity of the multi-wave signal emission element bracket is 34 degrees; the multi-wave signal emission element bracket is made from violet sand earthenware and manufactured by glazing a main body surface of the multi-wave signal emission element bracket and firing.

3. The multi-wave signal keep-fit energy chamber according to claim 1, wherein a power of the heating coils is 10-25 W.

4. The multi-wave signal keep-fit energy chamber according to claim 1, wherein the multi-wave signal waveguide cover is conical, is made of metals and has a height of 59-65 mm, a top diameter of 10-20 mm, a bottom diameter of 68-75 mm and a wall thickness of 1.5-3 mm; and an inner cone angle of the multi-wave signal waveguide cover is 34 degrees.

5. The multi-wave signal keep-fit energy chamber according to claim 1, wherein the multi-wave signal emission element base is made of plastics and has a diameter of 108-115 mm and a height of 107-115 mm; an inner wall of the base is a metal body; and the multi-wave signal emission element base is electrically connected with a 1000-3000 V high-voltage positive pole.

6. The multi-wave signal keep-fit energy chamber according to claim 1, wherein the coils or metal bodies coiled on the outer wall of the multi-wave signal emission element base have a height of 30-40 mm; and the carrier of the multi-wave signal charge has signal current of 2-3 mA and a voltage of 5-6 V.

7. The multi-wave signal keep-fit energy chamber according to claim 1, wherein the middle squirrel-cage chamber framework has a diameter of 800-900 mm and a length of 2000-2100 mm; and a movable bed is arranged in the center of the middle squirrel-cage chamber framework and has a length of 1800 mm-1900 mm.

8. The multi-wave signal keep-fit energy chamber according to claim 1, wherein the circuit control system of the multi-wave signal emission elements controls a temperature of the keep-fit energy chamber to be between 33° C. and 50° C. to serve as a stable operating interval.

9. The multi-wave signal keep-fit energy chamber according to claim 1, wherein the multi-wave signal modulation power supply comprises a negative pole made of magnesium and magnesium alloy sheets and further comprises a collector and a positive pole attached with a copper or silver foil on the collector, wherein the sheets have a thickness of 0.2-1 mm; a surface of each of the sheets is insulated; a voltage between the positive pole and the negative pole is 1.3-2 V; individual collector plates are superposed and connected with one another; and requirements of a signal current and a voltage of the carrier of the multi-wave signal charge are met.

10. The multi-wave signal keep-fit energy chamber according to claim 9, wherein the collector is manufactured in the following manner:

emulsifying the following nine materials: (1) 600 g of calcium chloride soaked into glue in 600 g of water; (2) 7000 g of 2% xanthan gum aqueous solution; (3) 1800 g of industrial salt; (4) 360 g of wool fat; (5) 360 g of glycerin; (6) 300 g of vegetable oil; (7) 600 g of water-soluble glue; (8) 1800 g of 10% glutinous rice flour paste and (9) 300 g of a lipophilic emulsifier, to get a emulsified mixture;

adding (10) 240 g of thorium oxide, (11) 240 g of iron phosphate, (12) 100 g of lithium cobalt oxides, (13) 100 g of lithium nickelate, (14) 4800 g of trisodium phosphate, (15) 300 g of industrial salt, (16) 800-1200 g of cobalt sulfate and (17) 3600-4100 g of graphite into the emulsified mixture, to get a resultant; and uniformly stirring the resultant by a stirrer, coating the stirred resultant on 20-30 g of paper with a thickness of 0.3-0.6 mm, drying, slicing and sizing the coated paper into pieces, adhering the pieces to the negative pole of the multi-wave signal modulation power supply with a corresponding size, performing vacuum treatment at a temperature of 40-70° C. for 1-2 hours, and drying.

11. The multi-wave signal keep-fit energy chamber according to claim 9, wherein multi-wave resonance is operatively generated between the multi-wave signal keep-fit energy chamber and an object disposed into the multi-wave signal keep-fit energy chamber.

* * * * *